United States Patent [19]

Levy et al.

[11] 4,332,244

[45] Jun. 1, 1982

[54] MASK FOR THE SAFE DELIVERY OF INHALATION GASES TO SMALL LABORATORY ANIMALS

[75] Inventors: David E. Levy; Alfred Zwies, both of New York; Thomas E. Duffy, Mamaroneck, all of N.Y.

[73] Assignee: The Government of the United States as represented by the Secretary of Department of Health and Human Services, Washington, D.C.

[21] Appl. No.: 195,188

[22] Filed: Oct. 8, 1980

[51] Int. Cl.[3] .............................................. A61M 16/00

[52] U.S. Cl. ............................... 128/205.25; 128/910; 128/206.28

[58] Field of Search .............. 128/910, 203.29, 205.25, 128/206.28

[56] References Cited

U.S. PATENT DOCUMENTS 2,960,985 11/1960 Wiese, Jr. ........................ 128/203.29

4,015,598 4/1977 Brown ............................ 128/205.25

*Primary Examiner*—Henry J. Recla

*Attorney, Agent, or Firm*—Holman & Stern

[57] ABSTRACT

An anesthesia mask for laboratory animals comprising a supply tube having a generally conical mask at one end into which the animal's snout is inserted. Pressurized anesthesia gas is delivered through the tube and is prevented from leaking into the ambient environment by means of a second tube which concentrically surrounds the supply tube and is annularly spaced therefrom so that the space can be evacuated by a vacuum source. A holding bar is slidable transversely into the mask to hook onto the animal's incisors.

7 Claims, 4 Drawing Figures

MASK FOR THE SAFE DELIVERY OF INHALATION GASES TO SMALL LABORATORY ANIMALS

TECHNICAL FIELD

The present invention relates to masks for delivering inhalation gases to small laboratory animals and, more particularly, to such masks which are suitable for the delivery of volatile anesthetic gases without danger to the animal or to personnel in the area.

BACKGROUND OF THE INVENTION

The use of volatile anesthetic gases offers considerable advantages over barbiturates for experimental studies requiring prolonged surgery in small laboratory animals. In particular, continuous control of the depth of anesthesia is more readily obtained with fact-acting inhalation gases than with barbiturates. In addition, animals recover quickly once the volatile type anesthetic gas is removed, thereby permitting early observation of the animal's behavior.

At the present time no satisfactory system exists for providing safe delivery of volatile anesthetics to small animals. For example, it is common to use the barrel of a syringe or a funnel-like mask to deliver anesthetic gases to the animal. The problem with such devices is that they permit the anesthetic gas to escape into the surrounding atmosphere. The volatility and toxicity of such gases present a considerable danger to the laboratory personnel working near the anesthetized animal. Moreover, the prior art devices used for this purpose are often applied too tightly to the animal, resulting in pressurization of the animal's lungs which could alter the pulmonary function.

It is therefore an object of the present invention to provide a mask for delivering inhalation gases to small animals which is safe for the animal and safe for personnel in the surrounding area.

SUMMARY OF THE INVENTION

In accordance with the present invention, an anesthesia mask includes a gas supply tube which terminates in one end in a frusto-conical nose cone adapted to receive the snout of an animal. The supply tube is concentrically surrounded by and annularly spaced from an exhaust tube. The end of the supply tube remote from the nose cone is connected to a source of pressurized anesthetic gas which is delivered to the supply tube and, in turn, to the nose cone. A vacuum or low pressure source is connected to the exhaust tube so that excess gas in the region of the nose cone may be vented instead of escaping into the surrounding atmosphere. In a preferred embodiment, a bar extends radially through an outer shell of the device into the general region of the nose cone where it can be adjusted so that animal's incisors can be hooked onto the bar to hold the animal in place. The loose fitting nature of the nose cone and exhaust tube prevents exposure of the animal to either negative or positive pressure which could alter the animal's pulmonary function.

BRIEF DESCRIPTION OF THE DRAWINGS

The invention will be better understood by referring to the accompanying drawings taken in conjunction with the description, wherein.

DESCRIPTION OF THE PREFERRED EMBODIMENTS

Figure 1:
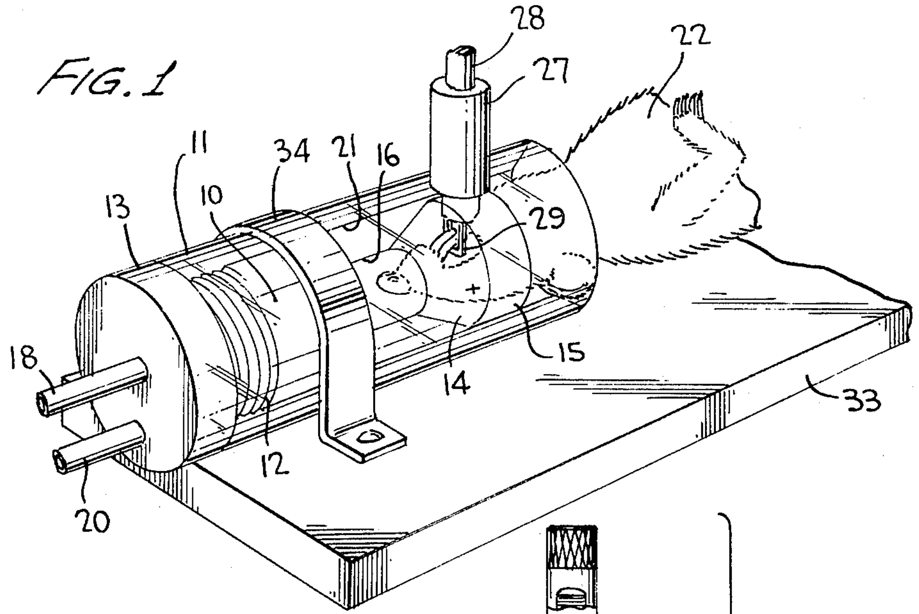
FIG. 1 is a view in perspective of the mask of the present invention in use.
Figure 2:
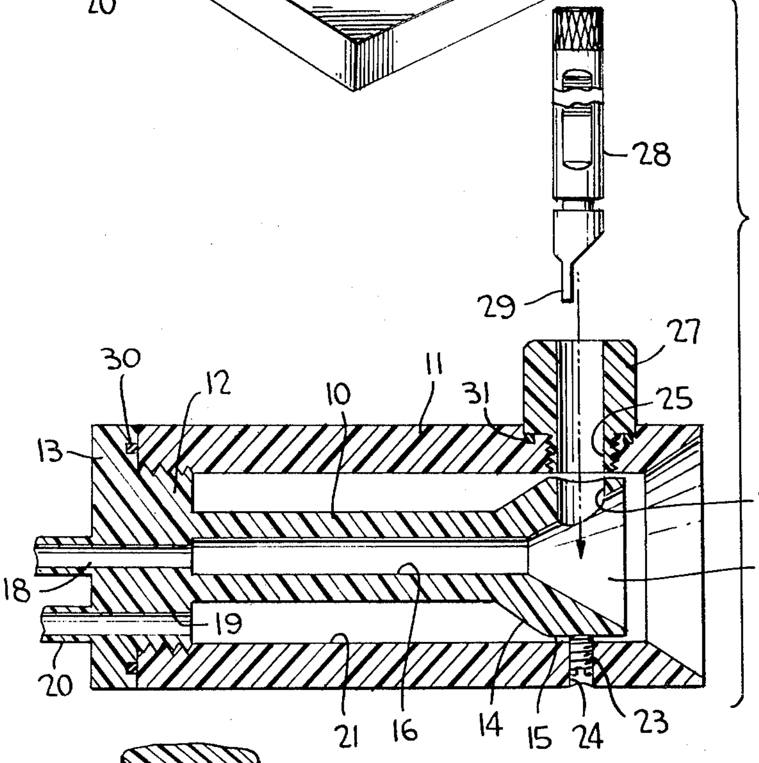
FIG. 2 is a elevation view in section, partially exploded of the mask of the present invention.
Figure 4:
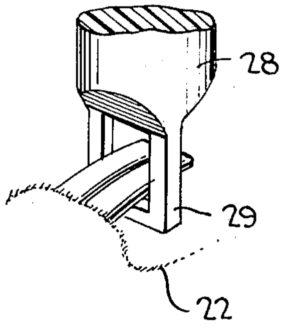
FIG. 4 is a detailed view in perspective of a portion of the mask illustrated in FIG. 1.
Figure 3:
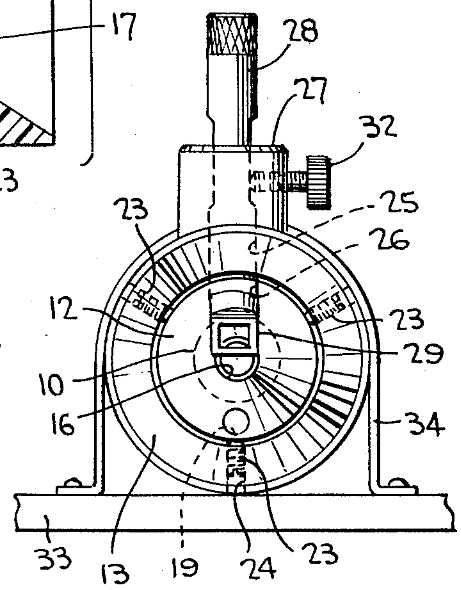
FIG. 3 is an end view of the mask of the present invention.

Referring to the drawings with greater specificity, the mask of the present invention is comprised primarily of two cylinders 10 and 11. For purposes of clarity and understanding of the present invention, cylinders 10 and 11 are illustrated as being made of clear plastic material; however, the mask may be made of opaque material which can be metal, plastic, or the like. Cylinder 10 includes a mid-portion of relatively small diameter which extends throughout most of the length of the cylinder. The left end (as viewed in FIG. 2) of cylinder 10, hereinafter referred to as the supply end, includes two larger-diameter cylindrical sections 12 and 13 wherein cylindrical section 13 has the larger diameter and is disposed at the extreme end of cylinder 10. Cylindrical section 12 is circumferentially threaded to permit engagement with an internally-threaded section of the interior of cylinder 11. The opposite or mask end of cylinder 10 includes a frusto-conical flared portion 14 which terminates in a cylindrical portion 15 of larger diameter than the main body of cylinder 10. The main body of cylinder 10 is provided with a central longitudinally extending bore 16 which includes a slightly smaller diameter portion extending through cylindrical sections 12 and 13 to the end of the cylindrical body. At the mask end of cylinder 10, bore 16 flares out into a conical section 17 which is coextensive with sections 14 and 15 of the cylinder. A supply tube 18 is inserted into bore 16 at the supply end of cylinder 10. A further bore 19 extends parallel to bore 16 through cylindrical sections 12 and 13 and is fitted with a tube 20.

Outer cylinder 11 has a substantially constant outer diameter throughout its length which is substantially equal to the diameter of cylindrical section 13 of cylinder 10. Cylinder 11 is open at both ends and it includes a longitudinally extending bore 21 of diameter slightly larger than the diameter of cylindrical section 15 of cylinder 10 and of substantially the same diameter as cylindrical section 12 of cylinder 10. The section of bore 21 is threaded proximate the supply end of cylinder 11 to engage the circumferential threads of cylindrical section 12. At the opposite or mask end of bore 21, the bore flares outwardly in a frusto-conical configuration.

Cylinder 10 is arranged to be inserted into bore 21 of cylinder 11 with the threaded portion of cylindrical section 12 engaging the threaded portion of bore 21. When fully inserted, cylinder 10 is annularly spaced from the interior wall of cylinder 11, the spacing being rather small in the region of cylindrical section 15. Cylindrical section 15 terminates interiorally of the open mask end of cylinder 11 such that the frusto-conical end of cylinder 11 aligns with the conical interior 17 of cylinder 10 to provide a mask-like region for receiving the snout of an animal 22. Cylindrical section 15 is supported in place by means of three set-screws 23 which extend through three circumferentially spaced radially-extending bores 24 defined through cylinder 11. Set-screws 23 are adjusted to maintain cylindrical section 15 annularly spaced from the interior wall of cylinder 11.

A radially extending bore 25 extends through cylinder 11 and is aligned with a similar radially extending bore 26 defined through cylindrical section 15 of cylinder 10 when cylinder 10 is fully inserted in cylinder 11. A collar member 27 is threadedly engaged in bore 25 and extends radially outward from cylinder 11. Collar member 27 includes a longitudinally extending bore which receives a rod 28 that is longitudinally movable within the bore by means of adjustment screw 32. The interior end of rod 28 terminates in an eye-like member 29 which extends into conical region 17 to engage the upper incisors of animal 22.

Supply tube 18 is connected to a pressurized source of anesthetic gas. Vacuum tube 20 is connected through vacuum or a source of negative pressure. In operation, the animal's snout is inserted into bore 16 through the flared region 17 and member 28 is lowered until the animal's incisors can be hooked in eye member 29. Anesthetic gas under pressure is then delivered via tube 18 through bore 16 wherein it is inhaled by the animal. Anesthetic gas which is not so inhaled is drawn through the annular space between cylinder 10 and cylinder 11 and out through vacuum connected tube 20. In this manner, escape of anesthetic gas into the surrounding environment is prevented, thereby affording a safe environment for laboratory personnel. In addition, the loose fitting nature of the mask assures that the animal is not exposed to either excessive positive or negative pressure which could alter the animal's pulmonary function. Depth of anesthesia is readily controlled on a continuous basis with short-acting inhalation gases, thereby permitting fast observation of the animal's behavior after the laboratory procedure is completed.

In a preferred embodiment, the cylinders 10 and 11 are made of Lucite whereas tubes 18 and 20 are made of stainless steel tubing. Member 28 is also made of stainless steel. These materials are by way of example only, and are by no means limiting on the scope of the invention.

Also, by way of example, in an actually constructed embodiment, cylinder 10 was machined from a 1 and $\frac{7}{8}$th inch diameter Lucite rod in which a $\frac{1}{4}$ inch diameter hole was drilled to form bore 16. The two stainless steel tubes 18 and 20 were $\frac{1}{4}''$ diameter tubes that were sealed by pressure into the delivery end of the cylinder. The flared portion 17 of cylinder 10 was constructed to provide a 1 and $\frac{1}{8}$th inch diameter for the base of the cone. An O-ring was placed between the mating surfaces of section 13 of cylinder 10 and the end of cylinder 11 in a suitably provided groove for purposes of pressure sealing the two cylinders at their abutting surfaces. Bore 25 in cylinder 11 is also surrounded by an O-ring 31 between it and collar 27 for purposes of providing a pressure seal. Thumb screw 32 is provided to tighten collar 27 against rod 28 in the desired position for and can be used for delivery of ether, methoxyflourane, halothane, variable carbon dioxide and oxygen concentrations, etc. Satisfactory anesthesia can be obtained with gases delivered at a flow rate of approximately 2 liters per minute. The unit may be scaled upward or downward in size to serve appropriately sized animals and to accommodate varying flow rates of anesthetic gases. With minor modifications, the present invention may also be used as a "brain blower" wherein it is important to extrude the brain rapidly in order to arrest cereberal metabolism while the animal continues to inspire a controlled gas mixture. The mask has proven to be convenient to use and minimizes the possibility of potentially harmful gases escaping into the laboratory environment.

The mask may be secured to a table or other supporting surface 33 by means of a strap 34 having a generally U-shape with flanges which may be bolted to element 33. Other means for securing the mask assembly to a supporting surface may also be employed.

The instant invention is not to be limited to the exact details of constructions and methods shwon and described, for obvious modifications can be made by a person skilled in the art.

The embodiments of the invention in which an exclusive property or privilege is claimed are as follows:

1. A mask for delivering anesthetic gas under pressure for inhalation by a laboratory animal, said mask comprising:

first and second hollow tubes, each having first and second ends, wherein said first tube is secured within said second tube in spaced relation from said second tube to define an aspiration chamber between the tubes, said first end of said first tube being longitudinally recessed from the first end of said second tube, said first tube having a snout-receiving means at its first end for receiving a snout of said laboratory animal in a loose fitting engagement, said snout-receiving means being surrounded by said aspiration chamber;

means for supplying said anesthetic gas under pressure to said snout-receiving means of said first tube; and means for aspirating gas from said aspiration chamber to prevent anesthetic gas which is not inhaled by said laboratory animal from leaking into the ambient environment.

2. The mask according to claim 1 wherein said first and second tubes have generally cylindrical shape and wherein said aspiration chamber is an annular space between said first and second tubes.

3. The mask according to claim 2 wherein said means for supplying comprises a tube for delivering said anesthetic gas under pressure connected to said second end of said first tube, and wherein said first tube includes a longitudinally extending bore through which said anesthetic gas flows from said second end of said first tube to said snout-receiving means.

4. The mask according to claim 3 wherein said second tube is provided with a longitudinally extending bore which defines said aspiration chamber with said first tube, said first end of said second tube surrounding said snout-receiving means of said first tube, and wherein said means for aspirating includes a tube connected to the longitudinally extending bore in said second tube and extends from said second end of said second tube.

5. A mask for delivering anesthetic gas under pressure for inhalation by a laboratory animal, said mask comprising:

first and second hollow tubes wherein said first tube is secured within said second tube in spaced relation from said second tube to define an aspiration chamber between the tubes, said first tube having a snout-receiving means for receiving a snout of said laboratory animal, said snout-receiving means being surrounded by said aspiration chamber;

means for supplying said anesthetic gas under pressure to said snout-receiving means of said first tube; and means for aspirating gas from said aspiration chamber to prevent anesthetic gas which is not inhaled by said laboratory animal from leaking into the ambient environment;

wherein said first and second tubes have generally cylindrical shape and wherein said aspiration chamber is an annular space between said first and second tubes, wherein said first cylinder has first and second ends, wherein said snout-receiving means is disposed at said first end, wherein said means for supplying comprises a tube for delivering said anesthetic gas under pressure connected to said second end, wherein said first tube includes a longitudinally extending bore through which said anesthetic gas flows from said second end to said snout-receiving means, wherein said second tube is provided with a longitudinally extending bore which defines said aspiration chamber with said first tube, said second tube having a first end which surrounds said snout-receiving means of said first tube and a second end, wherein said means for aspirating includes a tube connected to the longitudinally extending bore in said second tube and extends from said second end of said second tube, wherein said first tube includes a diametrically enlarged portion at said second end which is circumferentially threaded to engage a similarly threaded portion of said bore of said second tube and wherein said first end of said first tube is maintained spaced from said second tube by means of set screws extending through said second tube into contact with said first end of said first tube.

6. The mask according to claims 1 or 5 further comprising gripping means secured to said second tube for holding said laboratory animal in place in said snout-receiving means of said first tube.

7. The mask according to claim 6 wherein said gripping means includes transversely aligned bores in said first ends of said first and second tubes and a rod extending through said aligned bores into said snout-receiving means of said first tube, means supporting said rod on said second tube for longitudinal displacement through said aligned bores, said rod including an eye-like member for engaging the incisors of said laboratory animal in said snout-receiving means of said first tube.

* * * * *